United States Patent [19]

Chartrain et al.

[11] Patent Number: 5,491,077
[45] Date of Patent: Feb. 13, 1996

[54] MICROBIAL METHOD

[75] Inventors: Michel M. Chartrain, Westfield; Shieh-Shung T. Chen, Morganville; George M. Garrity, Westfield; Brian Heimbuch, North Brunswick; Christopher Roberge, Clark; Ali Shafiee, Westfield, all of N.J.

[73] Assignee: Merck & Co., Inc., Rahway, N.J.

[21] Appl. No.: 277,728

[22] Filed: Jul. 20, 1994

[51] Int. Cl.$^6$ .............................. C12P 17/16; C12P 17/12
[52] U.S. Cl. .............................. 435/118; 435/117; 435/122
[58] Field of Search .................................. 435/117, 118, 435/122

[56] References Cited

U.S. PATENT DOCUMENTS 5,270,324 12/1993 Zamboni et al. ...................... 514/311

FOREIGN PATENT DOCUMENTS 604114  6/1994  European Pat. Off. ..

OTHER PUBLICATIONS

Int'l. J. Syst. Bact. 43(3):549–554.
Bergey's Manual of Systematic Bacteriology vol. II 1320–22.
J. Org. Chem. 1993, 58, 3731–3735.

Primary Examiner—Herbert J. Lilling
Attorney, Agent, or Firm—Mollie M. Yang; David L. Rose

[57]  ABSTRACT

The present invention provides a process for the stereoselective reduction of phenylalkyl ketones to their corresponding (S)-hydroxy compounds. The process utilizes the novel microorganism Microbacterium MB 5614 to effectuate the chiral reduction. The present invention also provides said novel Microbacterium, which has been deposited with the ATCC and assigned the accession number ATCC 55557.

8 Claims, No Drawings

MICROBIAL METHOD

BACKGROUND OF THE INVENTION

The leukotrienes constitute a group of locally acting hormones, produced in living systems from arachidonic acid. The major leukotrienes are leukotriene $B_4$ (abbreviated as $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various disease states are also discussed in the book by Rokach.

There has been reported in U.S. Pat. No. 5,270,324 a class of quinoline type leukotriene antagonists, of which compounds having the formula (I) are a subset:

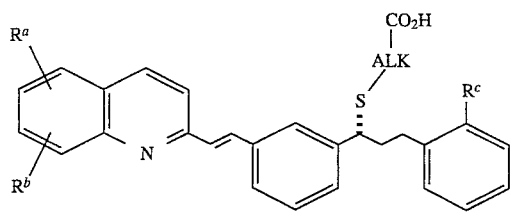

wherein $R^a$, $R^b$ are, inter alia, hydrogen or a halogen; and $R^c$ may be $CO_2R^d$, $COR^d$ or $C(R^e)_2$—OH; $R^d$ may be hydrogen or a lower alkyl, and $R^e$ may be lower alkyl; and ALK is for example cyclopropyl-1,1-(bis)methylene, isopropyl, and the like.

There is further disclosed in European Published Application 604114 leukotriene antagonists of which compounds having the formula (II) are a subset:

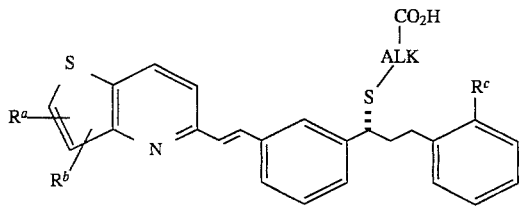

in which $R^a$, $R^b$, $R_c$ and ALK are as given above.

(S)-Hydroxy compounds of formula (III), infra, are intermediates in the synthesis of compounds of formulae (I) and (II). Compounds of formula (III) may be prepared from the corresponding ketones of formula (IV), infra, by using a chiral reducing agent such as diisopinocampheylchloroborane. The chemical chiral reduction generally requires the use of expensive chiral reducing agents; therefore, there exists a need for an alternative method for the preparation of chiral compounds of formula (III) that may be more economical and/or more convenient than the chemical method.

SUMMARY OF THE INVENTION

The present invention provides a stereoselective process for reducing a phenylalkyl ketone to the corresponding (S)-hydroxy derivative, which comprises contacting said phenylalkyl ketone with Microbacterium MB5614 having the identifying characteristics of ATCC 55557, or a mutant or a variant thereof. The present invention also provides a biologically pure culture of Microbacterium MB5614 (ATCC 55557), or a mutant or a variant thereof.

DETAILED DESCRIPTION OF THE INVENTION

In one aspect, the present invention provides a stereoselective process for reducing a phenylalkyl ketone to the corresponding (S)-hydroxy derivative, which comprises contacting said phenylalkyl ketone with Microbacterium MB5614 having the identifying characteristics of ATCC 55557, or a mutant or a variant thereof.

More particularly, the invention provides a process for the preparation of a compound of formula (III)

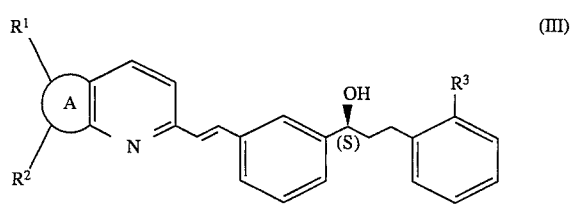

which comprises:

contacting a compound of formula (IV)

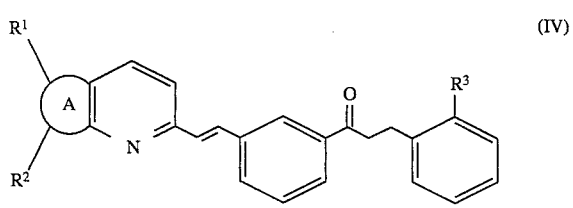

with Microbacterium MB5614 having the identifying characteristics of ATCC 55557, or a mutant or a variant thereof; wherein A is —CH=CH—S— or —CH=CH—CH=CH—;

$R^1$ and $R^2$ are independently hydrogen or a halogen;

$R^3$ is $CO_2R^6$, $COR^6$ or $C(R^7)_2$—O—$R^8$;

$R^6$ is hydrogen or lower alkyl;

$R^7$ is lower alkyl; and $R^8$ is hydrogen or a hydroxy protecting group.

In a preferred embodiment A is —CH=CH—CH=CH—, one of $R^1$ and $R^2$ is hydrogen and the other is a halogen, and $R^3$ is $CO_2R^6$.

In a more preferred embodiment A is —CH=CH—CH=CH—, one of $R^1$ and $R^2$ is hydrogen and the other is chlorine, and $R^3$ is $CO_2CH_3$.

In another aspect of the invention there is provided a biologically pure culture of the microorganism Microbacterium MB5614 having the identifying characteristics of ATCC 55557, or a mutant or a variant thereof.

Abbreviations and Definitions

In the application, unless specifically stated otherwise, the following abbreviations and definitions apply.

FAB-MS=fast atom bombardment mass spectrometry

HPLC=high pressure liquid chromatography

MES=N-morpholinoethanesulfonic acid

MSG=monosodium glutamate

NMR=nuclear magnetic resonance

TLC=thin-layer chromatography

UV=ultraviolet

"Alkyl" includes linear, branched and cyclic structures and combinations thereof.

"Lower alkyl" means alkyl groups of from 1 to 7 carbon atoms. Examples of lower alkyl groups include methyl, ethyl, propyl, isopropyl, butyl, s- and t-butyl, pentyl, hexyl, heptyl, cyclopropyl, cyclobutyl, cyclopentylmethyl, cyclohexyl, and the like.

"Halogen" includes fluorine, chlorine, bromine and iodine.

"Hydroxy protecting group" may be for example an ether such as methoxymethyl, tetrahydropyranyl, ethoxyethyl, trichloroethyl, t-butyl, allyl, benzyl, trimethylsilylethyl, diphenylmethyl, and triphenylmethyl; a silyl ether such as trimethylsilyl, dimethylisopropylsilyl, t-butyldimethylsilyl, and t-butyldiphenylsilyl; an ester such as formyl, trichloroacetyl, benzoyl, and trifluoroacetyl; a carbonate such as trichloroethyl, benzyl, and allyl. Other suitable hydroxy protecting groups may be found in standard references such as *Protective Groups in Organic Synthesis*, Green and Wuts, Eds., 1991, John Wiley & Sons, Inc, New York.

Utility

Compounds of formula (III) are intermediates in the preparation of leukotriene antagonists of formulae (I) and (II); the preparation of these leukotriene antagonists using such intermediates are disclosed in U.S. Pat. No. 5,270,324 and EP Published Application 604114, as well as co-pending U.S. application Ser. No. 08/174,931. Compounds of formulae (I) and (II) are useful as anti-asthmatic, anti-allergic, anti-inflammatory, and cytoprotective therapeutic agents.

Preparation of the Substrate

In the present process for microbial chiral reduction of ketones, the substrates for Microbacterium, compounds of formula (IV) may be prepared according to methods known in the art. Thus, preparation of compounds of formula (IV) wherein A is —CH=CH—CH=CH— is disclosed in U.S. Pat. No. 5,270,324; and preparation of compounds of formula (IV) wherein A is —S—CH=CH— is disclosed in European Published Application 604114.

Description of the Microorganism

Microbacterium MB5614 was isolated from a soil sample collected in a field at Santa Rosa Memorial Park, Guanacaste Pr., Costa Rica. The field had been subject to burning 48 hours prior to sampling. A sample of the culture has been deposited under the Budapest Treaty with the American Type Culture Collection, Rockville, Md., as ATCC 55557, and with the Merck Microbial Resources Culture Collection, Rahway, N.J., as MB5614.

In the following description, observations of growth and general cultural characteristics were carried out as described by Cure and Keddie, 1969, Methods For The Morphological Examination Of Aerobic Coryneform Bacteria. In Board and Lovelock (editors) *Sampling Microbiological Monitoring of Environments*. Academic Press, London, pp. 123–135. Carbon source utilization was conducted as described by Kamagata and Suzuki, 1986, In Sneath, P. H., N. S. Mair, M. E. Sharpe, and J. G. Holt (editors) *Bergey's Manual of Systematic Bacteriology*. V.II. pp. 1314. Other physiological tests were carded out as describe by Jones, 1975. A Numerical Taxonomic Study Of Coryneform And Related Bacteria. *J. Gen. Microbiol.* 87: 52–96. Cell wall analysis was done using the methods of Lechevalier and Lechevalier, 1980, The Chemotaxonomy Of Actinomycetes. In Dietz, A. and D. W. Thayer (editors) *Actinomyces Taxonomy*. Society for Industrial Microbiology, Arlington, Va. pp. 225–291; and Uchida and Aida, 1984, An Improved Method For The Glycolate Test For Simple Identification Of The Acyl Type Of Bacterial Cell Walls. *J. Gen. Appl. Microbiol.* 30: 131–134. Menaquinone analysis was done by the method of Hiraishi et al, 1992, Rapid Profiling Of Bacterial Quinones By Two-Dimensional Thin-Layer Chromatography. *Letter in Appl. Microbiol.* 14: 170–173. Fatty acid analysis was done by the method of Miller and Berger, 1985, Hewlett-Packard Application Note, pp. 228–241. Hewlett-Packard Co., Palo Alto, Calif.

Cell morphology. Non-motile, Gram positive, pleomorphic rod (1.14×0.38 μm) with coryneform morphology. Primary branching occurs during the growth cycle but without production of mycelia. A distinctive rod-coccus cycle does not occur. Endospores are not produced.

Cultural and physiological characteristics. Mesophilic, with growth occurring at 28° C. and 37° C. Thermoduric, with survival after heating for 30 min. at 60° C. Strict aerobe, catalase positive, oxidase negative. Metabolism is primarily respiratory; although it may also be fermentative. Acid is produced from cellobiose, fructose, galactose, D-glucose, glycerol, mannose, maltose, D-ribose, sucrose, trehalose, and D-xylose but not from D-arabinose, inositol, lactose, melibiose, D-raffinose, rhamnose, soluble starch, D-sorbitol, L-sorbose, or L-xylose. Gelatin is weakly hydrolyzed but chitin, starch, casein, urea, or cellulose are not. Nutrition is complex with growth occurring on peptone based media. B-complex vitamins and amino acids may be required for growth. On peptone based media colonies are 1–3 mm in diameter, yellow in color, transparent, raised, and have an entire edge. The surface glistens and the texture is mucoid. No diffusible pigments are produced.

Cell wall chemistry. The diamino acid in the cell wall is lysine. Glycine, alanine and glutamic acid are also present. The cell wall type is most likely B1α. Rhamnose is the major cell wall sugar with mannose, ribose, and an unidentified sugar ($R_{galactose}$=0.75) all present in lower concentration. The glycan moiety of the cell wall contains glycolyl residues. The major menaquinones are MK10 and MK11. The major fatty acids are $15:0_{anteiso}$, $17:0_{anteiso}$, and $16:0_{iso}$.

Chemotaxonomic studies reveal that MB5614 belongs to the genus Microbacterium; however, comparisons of the growth characteristics and patterns of carbohydrate fermentation are not consistent with the six currently recognized species of this genus (Table 1). On this basis, we propose a new species to accommodate this strain: *Microbacterium campoquemadoensis*.

TABLE 1

| Characteristics MB5614 | | | | |
|---|---|---|---|---|
| | | M. lacticum[1] | M. laevaniformans | M. imperiale[1] |
| Color: | yellow | yellow white | yellow | red orange |
| Production of acid from: | | | | |
| cellobiose | + | + | + | + |
| D-arabinose | − | − | − | + |
| D-raffinose | − | − | + | + |
| D-ribose | ± | ND | − | ND |
| D-sorbitol | − | ND | − | ND |
| D-xylose | + | − | − | + |
| fructose | + | + | + | + |
| galactose | + | + | + | + |
| glucose | + | + | + | + |
| glycerol | + | ND | + | ND |
| inositol | − | − | − | − |
| L-sorbose | − | − | − | − |
| L-xylose | − | ND | − | ND |
| lactose | − | + | −[3] | + |
| maltose | + | + | + | + |
| mannose | + | + | + | + |
| melibiose | − | ND | − | ND |

TABLE 1-continued

Characteristics MB5614

| | | | | |
|---|---|---|---|---|
| rhamnose | − | − | − | − |
| sol. starch | − | ND | + | ND |
| sucrose | + | − | + | + |
| trehalose | + | − | + | + |
| Hydrolysis of: | | | | |
| casein | − | ND | − | ND |
| cellulose | − | − | − | − |
| chitin | − | ND | ND | |
| gelatin | + | V | + | V |
| starch | − | + | + | V |
| urea | − | ND | ND | ND |
| Growth at 37° C.: | + | − | + | + |

| | M. dextranolyticum[2] | M. arborescens[2] | M. aurum[2] |
|---|---|---|---|
| Color: | yellow | orange | yellow |
| Production of acid from: | | | |
| cellobiose | + | ND | − |
| D-arabinose | − | + | − |
| D-raffinose | + | − | + |
| D-ribose | − | ND | − |
| D-sorbitol | ND | ND | ND |
| D-xylose | + | + | − |
| fructose | + | ND | + |
| galactose | + | ND | + |
| glucose | + | ND | + |
| glycerol | − | ND | − |
| inositol | − | ND | − |
| L-sorbose | − | ND | − |
| L-xylose | ND | ND | ND |
| lactose | + | ND | ND |
| maltose | + | ND | + |
| mannose | + | ND | + |
| melibiose | + | ND | − |
| rhamnose | − | ND | + |
| sol. starch | − | ND | + |
| sucrose | + | + | + |
| trehalose | + | ± | + |
| Hydrolysis of: | | | |
| casein | ND | ND | ND |
| cellulose | ND | ND | ND |
| chitin | ND | ND | ND |
| gelatin | − | + | + |
| starch | − | − | + |
| urea | − | ND | − |
| Growth at 37° C.: | − | − | + |

[1]Data taken from Yokota et al. 1993. Proposal of two new species of the genus Microbacterium: Microbacterium dextranolyticum sp. nov. and Microbacterium aurum sp. nov. Int. J. Syst. Bacteriol. 43(3): 549–554; and Collins and Keddie 1986. In Sneath, P. H., N. S. Mair, M. E. Sharpe, and J. G. Holt (editors) Bergey's Manual of Systematic Bacteriology. V. II. pp. 1320–1322.
[2]Data taken from Yokota et al.
[3]Reported as positive by Collins and Keddie
ND Not determined
V Variable Description of the Process The Microbacterium strain may be cultivated in a conventional medium containing known nutritional sources for growth of the bacteria, i.e., assimilable sources of carbon and nitrogen, with optional inorganic salts and other known growth factors added. The culture is preferably grown under submerged aerobic conditions; however, surface cultures and bottles may also be used for cultivation on a smaller scale. The general procedures used for the cultivation of other bacteria are applicable to the present invention.

The nutrient medium employed for the cultivation of Microbacterium should contain an appropriate assimilable carbon source, such as glucose, fructose, sucrose, and cellobiose. As a nitrogen source, ammonium chloride, ammonium sulfate, urea, ammonium nitrate, sodium nitrate, sodium glutamate, etc., may be used either alone or in combination with organic nitrogen sources, such as peptone, meat extract, yeast extract, corn steep liquor, soybean meal, cotton seed meal, etc. There may also be added, if necessary, nutrient inorganic salts to provide sources of sodium, potassium, calcium, ammonium, phosphate, sulfate, chloride, bromide, carbonate, zinc, magnesium, manganese, cobalt, iron, and the like.

The Microbacterium may be grown at any temperature suitable for satisfactory growth, e.g., 25°–40° C., and is most conveniently carried out at a temperature of around 27°–32° C. If fermentation is to be carried out in tank fermentors, it is desirable to use a vegetative inoculum in a nutrient broth from a slant culture or a lyophilized culture. After obtaining an active inoculum in this manner, it is aseptically transferred to the fermentation medium in a tank fermentor. Agitation in the tank fermentor is provided by stirring, and aeration may be achieved by injection of air or oxygen into the agitated mixture.

In one embodiment of the present process the ketone substrate (IV) is placed in contact with the Microbacterium being cultivated in an aqueous nutrient medium. The ketone substrate may be added to the Microbacterium culture at any time; but preferably, the substrate is added when sufficient biomass of the microorganism has been achieved. The biomass concentration can be easily monitored, for example by measuring the light absorbance at 660 nm of culture sample using a spectrophotometer. Typically, maximum biomass is reached about 3 to 5 days after inoculation. The bioconversion process may be monitored with conventional methods such as by HPLC followed by spectroscopic techniques. The level of the stereoselective reduction product reaches a maximum about 3 to 4 days after the addition of the substrate. The bioconversion of the ketone substrate to the corresponding (S)-hydroxy compound can be carried out on a continuous basis, for example for up to 500 hours, with the intermittent addition of the ketone substrate. The desired (S)-hydroxy compound thus produced may be recovered from the fermentation broth by any suitable methods for such recovery and separation; examples of these methods include extraction, precipitation, chromatography, and other art recognized conventional techniques.

In another embodiment of the present process, the ketone substrate is placed in contact with Microbacterium in a resting state. Resting state, as used herein, means that the microorganism is not actively growing but is capable of the desired function in buffered solution in the absence of supporting growth factors. Resting cells of Microbacterium are prepared by harvesting growing cells of Microbacterium, for example by centrifugation; the harvested cells may also be lyophilized, and then stored at −80° C. for future use. The resting cells are used as a cell suspension in an appropriate buffered solution such as phosphate or Tris buffer (pH 6–8). The ketone substrate is added to the cell suspension, and the mixture is incubated at a temperature of 20° to 40° C. to effect the reduction. Optionally, glucose can be added to the cell suspension to improve the efficiency of the bioconversion. Cells immobilized on support by physical adsorption or entrapment may also be used for the chiral reduction process. Cell immobilization may be achieved using conventional methods, for example, those reported in Karsten, G. and Simon, H., *Appl. Microb. Biotechnol.*, 1993, 38:441–446 and references cited therein.

It is to be understood that, for the biotransformation, the present invention is not limited to the particular organisms mentioned above but includes the use of variants and mutants thereof that retain the ketone reducing capability. Such variants and mutants can be produced from parent strains by various means, such as X-ray radiation, UV-radiation, and chemical mutagens, such as N-methyl-N'-nitro-N-nitrosoguanidine.

The following examples are provided to more fully illustrate the present invention, and are not to be construed as limiting the scope of the invention in any manner.

EXAMPLE 1

Seed culture of Microbacterium MB5614

A 1.5 ml frozen vial of Microbacterium MB5614 in SG medium (composition provided below in Example 4) was allowed to thaw at room temperature and then transferred to a 250 ml Erlenmeyer flask containing 50 ml of KE medium composed of (per liter of medium):

| | | |
|---|---|---|
| 10 g. | dextrin | |
| 5 g. | ardamine pH | |
| 5 g | NZ amine type E | |
| 3 g | beef extract | |
| 1 g | dextrose | |
| 0.37 g | $K_2HPO_4$ | |
| 0.05 g | $MgSO_4 \cdot 7H_2O$ | |
| q.v. 1 L | deionized water | |
| to pH 7.1 | NaOH | |
| 0.5 g | $CaCO_3$ | |

The flask was incubated for 24 hr at 28° C. on an orbital shaker at 220 rpm. A 1.0 ml aliquot of culture from the flask was then used to inoculate a 2.0 l Erlenmeyer flask containing 500 ml of KE medium. The 2.0 l flask was incubated for 24 hr at 28° C. on an orbital shaker at 220 rpm.

EXAMPLE 2

Bioconversion of methyl 2-(3-(3-(2-(7-chloro-2-quinolinyl)ethenyl)phenyl)- 3-oxopropyl)benzoate (hereinafter ketoester to methyl 2-(3-(3-(2-(7-chloro-2-quinolinyl)ethenyl)phenyl)-3(S)-hydroxypropyl)benzoate (hereinafter hydroxyester) (Method A)

A 2-ml aliquot of the seed culture of Example 1 was transferred into a 250-ml baffled flask containing 50 ml of bioconversion medium composed of (per liter of medium):

| | |
|---|---|
| 20 g | glucose |
| 5 g | soy meal |
| 5 g | yeast extract |
| 5 g | NaCl |
| 9.8 g | N-morpholinoethanesulfonic acid (MES) |
| q.v. 1 L | deionized water; pH adjusted to 7.0 |

A solution of the ketoester (5 mg) in acetone (0.5 ml) was added to the medium, and the flask was incubated at 27° C. on a shaker at 220 rpm in the dark. The bioconversion was monitored as follows: At various time intervals, 1 ml sample was taken from the flask and mixed with 1 ml of isopropanol. The resulting mixture was centrifuged after vortexing and an aliquot from the supernatant was examined by HPLC (Whatman Partisil 10 ODS-3 analytical column; eluant: linear gradient of acetonitrile in water (55%–95% in 30 min.); flow rate: 1 ml/min; column temp: 45° 1 C.).

EXAMPLE 3

Isolation and characterization of hydroxyester.

After 48 hrs of incubation, the biotransformation broth from 4 flasks were pooled (total 200 ml), and the pH adjusted to 6.0. The broth was centrifuged (20 min. at 3700 rpm) and the supernatant was recovered. The pellet was then suspended in 150 ml methanol and stirred for 30 min. in dark. The suspension thus obtained was centrifuged as above and the supernatant was again recovered. The pellet was extracted once more and the supernatant was pooled with those previously recovered.

The pooled extract was mixed with an equal volume of methylene chloride and, after vigorous shaking, the methylene chloride phase was recovered and dried under reduced pressure. The dried residue was applied to a semi-preparative silica gel plate and the plate was developed in a methylene chloride solvent system. The developed TLC plate was examined under UV light and a major UV-absorbing band with lower Rf value than the substrate was localized. The silica gel in this area was scraped off and was exhaustively extracted with methylene chloride. The extract was concentrated under reduced pressure and filtered.

The filtered extract was further purified by several injections onto a semi-preparative Whatman Partisil 10 ODS-3 (9.4 mm×25cm) column. This column was developed using similar conditions for the analytical column, except the flow rate was 3 ml/min (see Example 2). HPLC purified fractions were pooled and exhaustively extracted with methylene chloride. Methylene chloride extract was dried over $Na_2SO_4$ and concentrated to dryness under nitrogen to give 3.5 mg of the dried final product (direct HPLC quantitation of substrate and product shows between 30–40% conversion based on time of the harvest). NMR and FAB-MS spectral analysis established the product to be methyl 2-(3(S)-3-((2-(7-chloro-2-quinolinyl)ethenyl)phenyl)-3-hydroxy)propyl)benzoate, and chiral chromatography of HPLC purified fraction on Chiralcel OD column (eluant: 90% hexanes/isopropanol; flow rate: 2 ml/min; retention times: 17.9 min for (S)-hydroxyester, 19.8 min for (R)-hydroxyester) indicated an enantiomeric excess of 95%.

EXAMPLE 4

Bioconversion of ketoester to hydroxyester (Method B)

A 10 ml aliquot of the seed culture of Example 1 was used to inoculate a 2.0 l Erlenmeyer flask containing 500 ml of production medium (SG medium) composed of (per liter of medium):

| | |
|---|---|
| 0.5 g | $FeCl_3 \cdot 6H_2O$ |
| 30 g | dextrose |
| 20 g | monosodium glutamate (MSG) |
| 9.8 g | MES |
| 5 g | yeast extract |
| 5 g | NaCl |
| q.v. 1l | deionized water (pH7.0 NAOH) |

The flask was incubated at 28° C. on an orbital shaker at 200 rpm.

After the production culture had been incubated for 5 days, the ketoester (250 mg-in the form of 25 mg/ml solution in dimethylsulfoxide) was added. Additional lots of the ketoester (250 mg each) were added on days 8 and 9 post inoculation. The bioconversion to the hydroxyester was monitored by assaying the concentrations of ketoester and hydroxyester in the culture. Briefly, an aliquot of the culture broth was extracted with two volumes of ethyl acetate. The extract was then dried under nitrogen and resuspended in acetonitirile, and the solution was chromatographed on a Zorbax RX-C8 HPLC column (mobile phase: acetonitrile in water 10–90%, both acidified with 0.1% $H_3PO_4$; flow rate: 1.5 ml/min.). Retention time (ketoester)=5 min; retention time (hydroxyester)=12 min. Bioconversion under these conditions produced approximately 500 mg/l of the hydroxyester on day 10 post inoculation, at a rate of approximately 100 mg/( 1 day) during the reaction.

EXAMPLE 5

Bioconversion of ketoester to hydroxyester by resting cells of Microbacterium MB5614

Culture of Microbacterium MB5614 was grown according to the procedure described in Examples 1 and 2. Culture in the bioconversion medium was incubated for 44 hrs at 28° C. on an orbital shaker at 220 rpm, the cells were harvested by centrifugation at 15,000 rpm for 120 min. The resulting pellet was washed three times with 0.1M phosphate buffer, pH 7.2, lyophilized and stored at −80° C.

The cells were thawed, suspended in 4:5 g/volume of buffer, and the ketoester (5 mg/0.5 ml DMSO) was added to the cell suspension. The mixture was incubated at 27° C. The bioconversion was monitored as described above. After 40 hours of incubation greater than 50% conversion was observed (as determined by HPLC).

Addition of glucose (0.1M) to the cell suspension resulted in ca. 60% conversion after 40 hours of incubation.

What is claimed is:

1. A process for the preparation of a compound of formula (III)

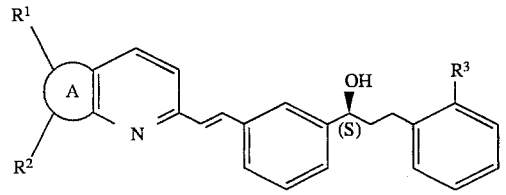

which comprises:

(1) contacting a compound of formula (IV)

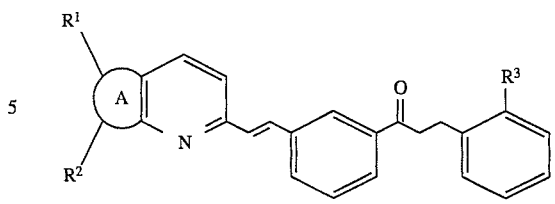

with Microbacterium MB5614 ATCC 55557, or a mutant thereof; and (2) isolating the compound of formula (III); wherein A is —CH=CH—S— or —CH=CH—CH=CH—CH—;

$R^1$ and $R^2$ are independently hydrogen or a halogen;

$R^3$ is $CO_2R^6$, $COR^6$ or $C(R^7)_2$—O—$R^8$;

$R^6$ is hydrogen or lower alkyl;

$R^7$ is lower alkyl; and $R^8$ is hydrogen or a hydroxy protecting group.

2. A process of claim 1 wherein A is —CH=CH—CH=CH—, one of $R^1$ and $R^2$ is hydrogen and the other is a halogen, and $R^3$ is $CO_2R^6$.

3. A process of claim 1 wherein A is —CH=CH—CH=CH—, one of $R^1$ and $R^2$ is hydrogen and the other is chlorine, and $R^3$ is $CO_2CH_3$.

4. A process of claim 1 wherein said Microbacterium is being cultivated in an aqueous nutrient medium containing assimilable carbon and nitrogen sources.

5. A process of claim 1 wherein said Microbacterium is in a resting state.

6. A process of claim 4 wherein said nutrient medium further contains $FeCl_3$.

7. A process of claim 4 wherein said nutrient medium further contains monosodium glutamate.

8. A process of claim 4 wherein said nutrient medium further contains $FeCl_3$ and monosodium glutamate.

* * * * *